United States Patent
Senetar

(10) Patent No.: US 7,132,580 B1
(45) Date of Patent: *Nov. 7, 2006

(54) SELECTIVE DIMETHYLETHER AND METHANOL RECOVERY AND RECYCLE IN A METHANOL-TO-OLEFIN PROCESS

(75) Inventor: John J. Senetar, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 617 days.

This patent is subject to a terminal disclaimer.

(21) Appl. No.: 10/436,628

(22) Filed: May 13, 2003

(51) Int. Cl.
C07C 1/20 (2006.01)
C07C 1/207 (2006.01)
C07C 7/10 (2006.01)

(52) U.S. Cl. ............. 585/639; 585/463; 585/833; 585/640; 585/809; 208/291; 208/332

(58) Field of Classification Search ........... 585/639, 585/469, 833, 640, 809; 208/291, 332
See application file for complete search history.

(56) References Cited

U.S. PATENT DOCUMENTS

| | | | |
|---|---|---|---|
| 4,387,263 A | 6/1983 | Vogt et al. .......... | 585/640 |
| 4,587,373 A | 5/1986 | Hsia ................. | 585/639 |
| 4,898,717 A * | 2/1990 | Hsia et al. .......... | 422/190 |
| 5,095,163 A | 3/1992 | Barger ............... | 585/640 |
| 5,126,308 A | 6/1992 | Barger et al. ........ | 502/214 |
| 5,177,279 A * | 1/1993 | Harandi ............. | 585/312 |
| 5,191,141 A | 3/1993 | Barger et al. ........ | 585/640 |
| 6,864,401 B1 * | 3/2005 | Van Egmond ........ | 585/639 |
| 6,872,867 B1 * | 3/2005 | Senetar ............. | 585/638 |

* cited by examiner

*Primary Examiner*—Tam M. Nguyen
(74) *Attorney, Agent, or Firm*—John G. Tolomei; Mark Goldberg

(57) ABSTRACT

An improved methanol-to-olefin (MTO) product recovery scheme is provided which enables substantial reduction in the amount of light olefins that are undesirably captured in a dimethylether (DME) recycle stream and improved recovery of methanol when a portion of the methanolic feed to the MTO reaction zone is used as the scrubbing solvent in a primary DME absorption zone in order to recycle this DME oxygenate by-product to the MTO reaction zone. In accordance with the present invention, a liquid solvent stream recovered from the primary DME absorption zone is subjected in a stripping zone to light olefin stripping conditions sufficient to lift a substantial portion of the light olefins that are absorbed in the DME solvent without stripping a significant portion of this methanol solvent, thereby increasing the recovery of desired light olefins while simultaneously diminishing the amount of light olefins carried by the DME recycle stream back to MTO conversion step.

17 Claims, 2 Drawing Sheets

SELECTIVE DIMETHYLETHER AND METHANOL RECOVERY AND RECYCLE IN A METHANOL-TO-OLEFIN PROCESS

FIELD OF THE INVENTION

The present invention relates to the selective recovery and recycle of dimethylether (DME) and methanol from the effluent stream from a methanol-to-olefin (MTO) catalytic conversion process. The present invention relates more specifically to control of the undesired $C_2$ and $C_3$ olefin content of the principal DME recycle stream which has been found to be a detrimental effect of prior art methods for performing this recovery and recycle of DME.

BACKGROUND OF THE INVENTION

A major portion of the worldwide petrochemical industry is concerned with the production of light olefin materials and there subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. For various reasons including geographical, economic, political and diminished supply considerations the art has long sought a source other than petroleum for the massive quantities of raw materials that are needed to supply the demand for these light olefin materials. In other words, the holy grail of the R & D personnel assigned to work in this area is to find a way to effectively and selectively use alternative feedstocks for this light olefin production application thereby lessening dependence of the petrochemical industry on petroleum feedstocks. A great deal of the prior art's attention has been focused on the possibility of using hydrocarbon oxygenates and more specifically methanol as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol from these types of raw materials is well established and typically involves the use of one or more of the following procedures: (1) manufacture of synthesis gas by any of the known techniques typically using a nickel or cobalt catalyst followed by the well-known methanol synthesis step using relatively high pressure with a copper-based catalyst; (2) selective fermentation of various organic agricultural products and by-products in order to produce oxygenates; or (3) various combinations of these techniques.

Given the established and well-known technologies for producing oxygenates from alternative non-petroleum raw materials, the art has focused on different procedures for catalytically converting oxygenates such as methanol into the desired light olefin products. These light olefin products that are produced from non-petroleum based raw materials must of course be available in quantities and purities such that they are interchangeable in downstream processing with the materials that are presently produced using petroleum sources. Although many oxygenates have been discussed in the prior art, the principal focus of the two major routes to produce these desired light olefins has been on methanol conversion technology primarily because of the availability of commercially proven methanol synthesis technology. A review of the prior art has revealed essentially two major techniques that are discussed for conversion of methanol to light olefins. The first of these MTO processes is based on early German and American work with a catalytically conversion zone containing a zeolitic type of catalyst system. Representative of the early German work is U.S. Pat. No. 4,387,263 which was filed in May of 1982 in the U.S. without a claim for German priority. This '263 patent reports on a series of experiments with methanol conversion techniques using a ZSM-5-type of catalyst system wherein the problem of DME recycle is a major focus of the technology disclosed. Although good yields of ethylene and propylene were reported in this '263 patent, they unfortunately were accompanied by substantial formation of higher aliphatic and aromatic hydrocarbons which the patentees speculated might be useful as an engine fuel and specifically as a gasoline-type of material. In order to limit the amount of this heavier material that is produced, the patentees of the '263 patent propose to limit conversion to less than 80% of the methanol charged to the MTO conversion step. This operation at lower conversion levels necessitated a critical assessment of means for recovering and recycling not only unreacted methanol but also substantial amounts of a DME intermediate product. The focus then of the '263 patent invention was therefore on a DME and methanol scrubbing step utilizing a water solvent in order to efficiently and effectively recapture the light olefin value of the unreacted methanol and of the intermediate reactant DME.

This early MTO work with a zeolitic catalyst system was then followed up by the Mobil Oil Company who also investigated the use of a zeolitic catalyst system like ZSM-5 for purposes of making light olefins. U.S. Pat. No. 4,587,373 is representative of Mobil's early work and it acknowledged and distinguished the German contribution to this zeolitic catalyst based MTO route to light olefins. The inventor of the '373 patent made two significant contributions to this zeolitic MTO route the first of which involved recognition that a commercial plant would have to operate at pressure substantially above the preferred range that the German workers in this field had suggested in order to make the commercial equipment of reasonable size when commercial mass flow rates are desired. The '373 patent recognized that as you move to higher pressure for the zeolitic MTO route in order to control the size of the equipment needed for commercial plant there is a substantial additional loss of DME that was not considered in the German work. This additional loss is caused by dissolution of substantial quantities of DME in the heavy hydrocarbon oil by-product recovered from the liquid hydrocarbon stream withdrawn from the primary separator. The other significant contribution of the '373 patent is manifest from inspection of the flow scheme presented in FIG. 2 which prominently features a portion of the methanol feed being diverted to the DME absorption zone in order to take advantage of the fact that there exist a high affinity between methanol and DME thereby downsizing the size of the scrubbing zone required relative to the scrubbing zone utilizing plain water that was suggested by the earlier German work.

Primarily because of an inability of this zeolitic MTO route to control the amounts of undesired $C_4^+$ hydrocarbon products produced by the ZSM-5 type of catalyst system, the art soon developed a second MTO conversion technology based on the use of a non-zeolitic molecular sieve catalytic material. This branch of the MTO art is perhaps best illustrated by reference to UOP's extensive work in this area as reported in numerous patents of which U.S. Pat. No.

5,095,163, U.S. Pat. No. 5,126,308 and U.S. Pat. No. 5,191,141 are representative. This second approach to MTO conversion technology was primarily based on using a catalyst system comprising a silicoaluminophosphate molecular sieve (SAPO) with a strong preference for a SAPO species that is known as SAPO-34. This SAPO-34 material was found to have a very high selectivity for light olefins with a methanol feedstock and consequently very low selectivities for the undesired corresponding light paraffins and the heavier materials. This SAPO catalyzed MTO approach is known to have at least the following advantages relative to the zeolitic catalyst route to light olefins: (1) greater yields of light olefins at equal quantities of methanol converted; (2) capability of direct recovery of polymer grade ethylene and propylene without the necessity of the use of extraordinary physical separation steps to separate ethylene and propylene from their corresponding paraffin analogs; (3) sharply limited production of by-products such as stabilized gasoline; (4) flexibility to adjust the product ethylene-to-propylene weight ratios over the range of 1.5:1 to 0.75:1 by minimal adjustment of the MTO conversion conditions; and (5) significantly less coke make in the MTO conversion zone relative to that is experienced with the zeolitic catalyst system.

Despite the promising developments associated with the SAPO catalyzed MTO route to light olefins, the problem of DME co-production is common to both types of catalytic MTO routes discussed above and various measures have been suggested in the prior art to recover and recycle DME from the effluent stream from an MTO conversion zone. In U.S. Pat. No. 4,387,263, a relatively high pressure DME absorption zone is taught utilizing a plain water solvent in order to recapture and recycle the DME intermediate. By the use of the term "high pressure" with reference to this '263 patent, it is pointed out that the examples 1, 2, 3 and 4 were run at 2000 kPa (290 psi) and the fifth example was run at an even higher pressure of 4000 kPa (580 psi). One of the improvements suggested by U.S. Pat. No. 4,587,373 focused on utilizing a more efficient DME solvent in the DME absorption zone and recommended that a portion of the methanolic feed to the MTO conversion reactor be diverted to the DME absorption zone in order to more efficiently recapture the DME contaminant from the olefin product stream. As explained above, this '373 patent proposed to reduce commercial plant size by operating the MTO conversion reactor at a much higher preferred pressure than was suggested by the prior art and specifically focused on a reactor operation at about 550 kpa (80 psi) but noted that operating the MTO reactor at this high pressure would open the door to substantial DME loss in the heavy hydrocarbon product stream recovered from the principal separator in the effluent work-up portion of the flow scheme unless steps were taken to strip dissolved DME from the heavy hydrocarbon by-product stream. In particular, in the flow scheme of FIG. 2 of the '373 patent, it is proposed to strip the heavy hydrocarbon by-product recovered from the primary separator 16 in stabilizer tower 26 in order to recapture the value of the DME intermediate dissolved therein while simultaneously using a methanol solvent in the DME absorber 22.

In my attempts to practice a product recovery flow scheme quite similar to that disclosed in FIG. 2 of the '373 patent in conjunction with the use of a SAPO-type catalytic system in a MTO conversion zone, I have now found a further problem associated with the use of this flow scheme in order to recapture and recycle the DME intermediate that contaminants the effluent stream from the MTO reaction zone. I have found more specifically that if a portion of the methanol feed to the MTO conversion zone is diverted to the DME absorber as suggested in the '373 patent in order to recover DME more efficiently, there is substantial co-absorption of light olefins into the methanol solvent associated with this scheme. A methanol solvent's ability to extract from the light olefin-containing input stream to the DME absorber not only DME but substantial quantities of $C_2$ and $C_3$ olefins was not reported in the '373 patent and greatly complicates the design of an efficient product work-up flow scheme for a SAPO based MTO conversion zone. For example, when the DME absorption zone is operated with a methanol solvent at scrubbing conditions including a temperature of about 54° C. (129° F.) and a pressure of about 2020 kPa (293 psi) with a 99.85 mass-% methanol solvent, at least 12.3 mass-% of the $C_2$ olefins and 40.3 mass-% of the $C_3$ olefins charged to the DME scrubber will be co-absorbed in the DME-rich liquid solvent bottom stream withdrawn from the scrubber. When this DME-rich solvent stream is recycled to the MTO conversion zone, a substantial internal circuit of light olefins is created which acts to substantially increase the size of the MTO conversion zone while increasing the rate of detrimental coking on the catalyst contained therein due to the fact that these $C_2$ and $C_3$ olefins are reactive and can undergo polymerization and condensation to form coke precursors.

The problem addressed by the present invention is therefore to substantially diminish this undesired buildup of $C_2$ and $C_3$ olefins in the DME recycle stream flowing to the MTO conversion zone when methanol is used as a solvent in a DME absorption zone that is a prominent feature of an MTO reactor effluent work-up scheme.

SUMMARY OF THE INVENTION

The primary object of the present invention is to make the recovery and recycle of DME, methanol and/or other oxygenates found in an effluent stream from an MTO conversion zone more selective relative to the DME recovery technology taught in the prior art, thereby enabling a reduction in size of the MTO conversion zone due to the decrease in the amount of the DME recycle stream. A secondary objective is to provide a selective method of recovery and recycle of the DME intermediate found in the effluent stream from an MTO conversion zone which selective method substantially diminishes the risk of causing substantial coking on the catalyst system used in the MTO conversion zone due to internal recycle of relatively large amounts of very reactive light olefins and dienes.

This problem of light olefin contamination of the methanolic solvent recycle stream is addressed by the present invention by providing a specially designed stripping zone that is applied to the rich solvent stream recovered from the primary DME absorption zone in order to selectively remove substantial quantities of light olefins therefrom without significantly affecting the methanol content thereof, thereby substantially diminishing the risks of adverse effects on the performance of the MTO conversion zones when it is operated in an integrated manner with a reactor effluent product work-up flow scheme.

I have now found that the problem of light olefin contamination of the principal oxygenate recycle stream containing both DME and methanol that is a prominent feature of the MTO product work-up flow scheme that is taught in U.S. Pat. No. 4,587,373 can be efficiently solved by adding a special purpose light olefin stripper to the flow scheme of the '373 patent. This stripper operates on the liquid solvent bottom stream from the DME absorber and is designed to run at a severity such that a substantial portion of the light olefins dissolved in this liquid stream are stripped therefrom without lifting a major portion of the oxygenates such as DME and methanol that are contained in this stream. The flow scheme of the '373 patent suggests that this oxygenate-rich liquid stream should be subjected to an oxygenate stripping step which is designed to lift essentially all of the oxygenates contained therein. This of course differs sharply from the solution embedded in my invention which is based on the premise that these light olefins can be stripped selectively if the stripping severity level is adjusted so that it is not severe enough to lift a significant portion of the methanol contained in this liquid solvent stream but is at a level which will lift substantially 90 to 100% of the ethylene dissolved in this solvent stream and approximately 40 to 70% of the propylene.

The present invention is therefore a novel method of selective recovery of a DME-containing recycle stream and a DME-lean, methanol-lean and a light olefin-rich product stream from the effluent stream from a MTO conversion zone which effluent stream contains by-product water, unreacted methanol, a DME intermediate reactant, ethylene, propylene, $C_4$ to $C_6$ olefins, and minor amounts of other hydrocarbons and oxygenates. In accordance with a first embodiment of the present invention, the first step of this method involves cooling and separating at least a portion of this effluent stream into an aqueous liquid stream containing methanol and DME, a hydrocarbon liquid stream containing methanol, DME, and $C_2$ to $C_6$ olefins and a hydrocarbon vapor stream containing DME, methanol, ethylene and propylene. In the second step of this method, DME is stripped from the liquid hydrocarbon stream recovered in the first step in a DME stripping zone operated at stripping conditions effective to produce an overhead vapor stream containing DME, methanol, ethylene and propylene and a liquid hydrocarbon bottom stream containing $C_4$ to $C_6$ olefins. In the next steps of the instant method, the hydrocarbon vapor stream separated in the first step is combined with at least a portion of the overhead vapor stream produced in the DME stripping step to form a DME-rich light hydrocarbon vapor stream which is then charged to a primary DME absorption zone and therein countercurrently contacted with a DME selective solvent containing methanol at scrubbing conditions effective to produce: (1) a liquid solvent bottom stream containing methanol, DME, water and substantial and undesired amounts of ethylene and propylene (2) a light olefin-rich, DME-lean overhead vapor stream containing methanol. At least a portion of the liquid solvent bottom stream recovered from the DME scrubbing step is then passed to a light olefin stripping zone operating at stripping conditions effective to strip at least a substantial portion of the ethylene and propylene contained in this solvent stream without stripping any significant portion of the methanol therefrom to produce a stripper overhead stream rich in ethylene and propylene and containing trace amounts of DME and a liquid solvent bottom stream containing DME, methanol, water and reduced amounts of light olefin relative to the light olefin content of the liquid solvent bottom stream recovered from the primary DME scrubbing step. At least a portion of the liquid solvent bottom stream recovered from the light olefin stripping step is then recycled to the MTO conversion zone thereby selectively providing additional oxygenate reactants thereto. In the last step at least a portion of the overhead vapor stream produced in the primary DME absorption zone and at least a portion of the stripper overhead stream from the light olefin stripping zone are charged to a secondary DME absorption zone wherein these vapor streams are countercurrently contacted with an aqueous solvent at scrubbing conditions selected to produce a DME-lean and methanol-lean overhead vapor product stream containing ethylene and propylene and a bottom stream containing DME, methanol and the aqueous solvent.

A second embodiment involves the method of the first embodiment wherein at least a portion of the aqueous stream separated in the first step is combined with at least a portion of the bottom stream from the secondary DME absorption zone and charged to an oxygenate recovery zone operated at oxygenate stripping conditions effective to produce an overhead vapor stream rich in methanol and DME and an aqueous bottom stream which is substantially free of oxygenates and wherein at least a portion of this overhead vapor stream is recycled to the MTO conversion zone thereby providing additional oxygentate reactants thereto.

Yet another embodiment of the instant invention involves a further modification to the selective DME and methanol recovery methods described above in the first or second embodiments wherein the stripping conditions utilized in the light olefin stripping step include a severity level sufficient to produce a liquid solvent bottom stream containing less than 1 mass-% ethylene.

A further embodiment involves a modification of the DME and methanol recovery method described above is the second embodiment wherein the aqueous solvent stream charged to the secondary DME absorption zone is at least a portion of the aqueous bottom stream produced in the oxygenate recovery zone.

BRIEF DESCRIPTION OF THE DRAWINGS

FIG. 2 is a process flow diagram for a DME recovery scheme of the prior art. Not shown in these drawings are items of equipment that are well known to those of ordinary skill in the art such as heaters, coolers, heat exchangers, pumps, compressors, suction drums, knock out pots, condensers, overhead or bottom receivers, controls, valves, reboilers and the like.

TERMS AND CONDITIONS DEFINITIONS

Figure 1:
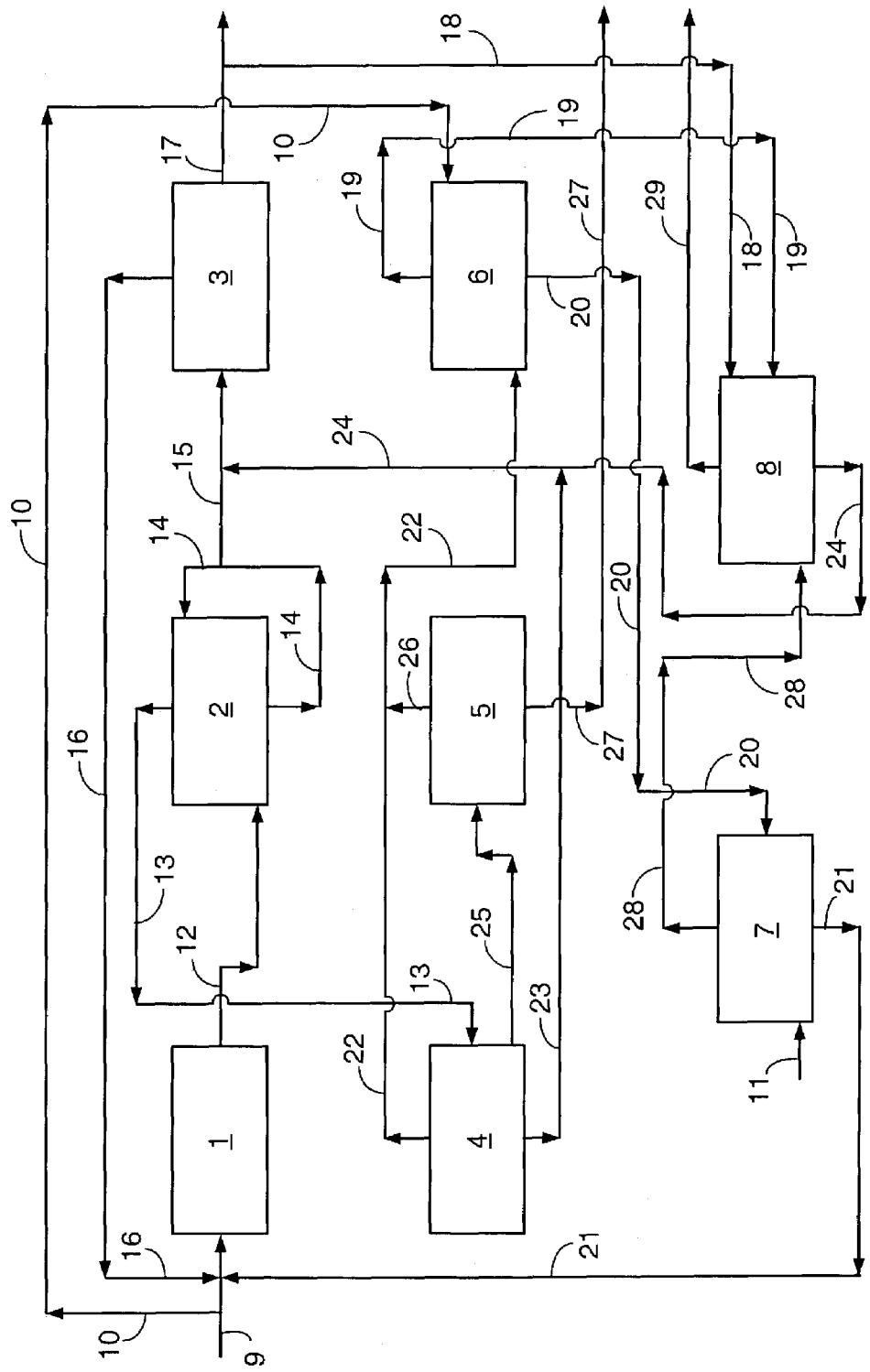
FIG. 1 is a process flow diagram of a preferred embodiment of the present invention, which portrays the essential interconnections and interrelationships between the operating zones associated with the instant selective DME and methanol recovery method.

The following terms and conditions are used in the present specification with the following meanings: (1) a "portion" of a stream means either an aliquot part that has the same composition as the whole stream or a part that is obtained by eliminating a readily separable component therefrom (e.g. if the stream contains hydrocarbons in admixture with steam, then after condensation of a major portion of the steam, it comprises an aqueous portion and a hydrocarbon portion); (2) an "overhead" stream means the net overhead recovered from the specified zone after recycle of any portion to the zone for reflux or any other reason; (3) a "bottom" stream means the net bottom stream from the specified zone obtained after recycle of any portion for purposes of reheating and/or reboiling and/or after any phase separation; (4) a line is "blocked-off" when it contains a valve that is set to a position that prevents flow through the line; (5) presence of necessary compressors and/or pumps is understood when flow is shown from a zone of relatively low pressure to a zone of higher pressure; (6) presence of necessary heating and/or cooling means is implied when flow is shown between zones operating at different temperatures; (7) an ingredient is "lifted" or "stripped" when it is concentrated in the overhead stream withdrawn from the specified zone; (8) a "vapor" stream means a stream containing one or more components in the gaseous state; (9) the term "light olefins" means ethylene, propylene and mixtures thereof and (10) the term "theoretical plates" as used herein means to the number of contacting stages required for a given mass transfer separation that is obtained utilizing the McCabe-Thiele assumptions and solution method see Perry, John H. *Chemical Engineer's Handbook*, 4$^{th}$ Ed (New York: McGraw-Hill, 1963), p. 13–22.

DETAILED DESCRIPTION OF THE INVENTION

The starting point for the present invention is a MTO conversion step which utilizes methanol as the principal source of the oxygenate reactant. As explained hereinbefore, there are essentially two different approaches to the catalytic conversion of methanol to light olefins. The principal distinction between these two approaches is based on the type of molecular sieve which is used as the active ingredient in the MTO catalyst system and I prefer the non-zeolitic route to MTO conversion. The details associated with this non-zeolitic route to MTO conversion are summarized in U.S. Pat. No. 5,095,163, U.S. Pat. No. 5,126,308 and U.S. Pat. No. 5,191,141, all of the teachings of which are all specifically incorporated herein by reference. As indicated in these teachings, the preferred molecular sieve is a silicoaluminophosphate system which has been established as occurring in numerous specific crystal structures. As is indicated in the cited patents, the most preferred SAPO structure for MTO conversion has been identified as a SAPO-34 structure. Although the selective recovery method of the present invention will work equally well with effluent streams from MTO conversion zones that contain zeolitic or non-zeolitic catalyst systems, it is preferred that the effluent stream be derived from an MTO conversion zone that is run with a SAPO-34 catalyst system. The SAPO-34molecular sieve maybe used alone or may be mixed with a binder and/or filler and formed into shapes such as extrudates, pills, spheres, and the like. Any of the inorganic oxide well known in the art maybe used as a binder and/or filler such as alumina, silica, alumina-phosphate, silica-alumina, and/or one of the various silica-rich clays that are well known to those of ordinary skill in the art. When a binder and/or filler is used in formulating the SAPO-34 catalyst system, SAPO-34 will usually be present in an amount of about 5 to 90 mass-% of the finished catalyst and preferably about 5 to 40 mass-% thereof. It is to be understood that the active ingredient is the SAPO-34 molecular sieve and the binder and/or filler is an inert material that is used to provide structural integrity to the catalyst particles. Best practice with a SAPO-34 catalyst system is to utilize it in a particle size suitable for a fluidized reactor system—typically an average particle size of 65 to 85 microns.

Although the MTO conversion zone can be operated with any of the reactor configurations known to the art, it is preferred to use a dynamic bed system instead of a fixed bed system in order to efficiently contact the methanol feed stream with the catalyst particles and facilitate the regeneration of the resulting coked catalyst. Either a moving bed system or a fluidized bed system may be used with good results. Best practice is however to use a fluidized bed catalyst system.

The fluidized MTO reaction zone is operated at conditions, which include a temperature of about 300° to 600° C. (572° to 1112° F.) with the preferred range being about 450° to 550° C. (842° to 1022° F.). The pressure used in the MTO conversion step is typically in the range of about 138 to 1000 kPa (20 to 145 psi) and preferably from about 170 to 345 kPa (24.7 to 50 psi). The contact time of the reactants with the catalyst is ordinarily measured in terms of a Weight Hourly Space Velocity (WHSV) calculated on the basis of a mass hourly flow rate of the sum of the mass of the methanol reactant passed to the MTO conversion zone, any other oxygenate reactants present in the feed or recycle and any hydrocarbon materials present therein divided by the mass of the SAPO-34 molecular sieve present in the MTO conversion zone. WHSV for use in the MTO conversion zone associated with the present invention can range from 1 to about 100 hr$^{-1}$, with the best results obtained in the range of about 5 to 20 hr$^{-1}$. Since the MTO conversion reaction is strongly exothermic, a significant temperature increase will occur across the reaction zone ordinarily of the magnitude of about 250° to 500° C. (482° to 932° F.). In a fluidized reactor system a catalyst circulation rate between the reactor and the regenerator will be set at a minimum level desired to hold average coke on the circulating inventory of the preferred SAPO catalyst in a range of about 1 to 20 mass-% of the active ingredient in the catalyst and, more preferrably, in the range of about 5 to 17 mass-%.

The regeneration step associated with the MTO conversion step will ordinarily use one of the established oxidative techniques for removing the necessary amount of coke from the catalyst prior to recirculation to the conversion zone. The primary factor that will establish the circulation rate between the conversion zone and the regeneration zone is the equilibrium value of coke on catalyst that it is desired to maintain in order to obtain the desired conversion level. SAPO-34 based catalyst system runs quite successfully at conversion levels of 95% or higher and results in a coke make of approximately 2 to 5 mass-% of methanol equivalents charged to the MTO conversion step. Knowing the coking rate someone of ordinary skill in the art can then establish a circulation rate to the regenerator based on burning coke at a rate which holds the overall average coke level on the circulating catalyst system used in the MTO conversion zone in the desired range specified hereinbefore. In comparison with traditional FCC operation, the circulation rate for an MTO fluidized conversion zone will be quite low since the regenerated catalyst is not needed to supply heat to the MTO reaction zone.

The methanol feedstock that is charged to the MTO conversion step can ordinarily be used with a diluent as is taught in the prior art acknowledged and incorporated above; however, best practice is not to use a diluent other than autogenously produced steam. The use of a diluent is beneficial in the sense of controlling the partial pressure of the methanol reactant but is disadvantageous in the sense of increasing the volume of the reaction zone and providing additional material that has to be separated from the products in the recovery section of the process. When a diluent is present in the MTO conversion step, it is preferably steam that is derived from the water that is an evitable contaminant of the methanol feed stream as well as of the recycle oxygenate streams. Since in many cases it is desired to charge a crude methanol feed stream containing up to about 20 wt-% water, there may in fact be substantial diluent that is brought into the system with the feed stream. In most cases however, it is preferred to run with a methanol feed stream that is 95 to 99.9 mass-% methanol. It is to be recognized that a substantial amounts of a steam diluent will be autogenously generated in the MTO conversion zone due to the fact that methanol can be calculated to contain over 56 mass % bound water and due to the fact that the kinetics of the reaction occurring in the MTO reaction zone are such that the initial formation of DME is extremely fast and results in the formation of one mol of a steam diluent for every 2 mols of methanol that react to produce DME.

The effluent stream withdrawn from an MTO conversion zone will therefore contain substantial amounts a water by-product as well as unreacted methanol, substantial quantities of DME intermediate, ethylene, propylene, $C_4$ to $C_6$ olefins and minor amounts of other hydrocarbons and oxygenates. Typically, with the preferred SAPO-34 catalyst system when it is run at 97+ conversion levels, approximately 70 to 78% of the methanol equivalent carbon entering the conversion step will be converted to the desired $C_2$ and $C_3$ olefins with 2 to 5% of the carbon converted to coke and approximately 0.5 to 1% converted to DME. The level of saturated hydrocarbons produced in the MTO conversion step such as methane, ethane and propane are characteristically held at very low levels with a SAPO-34 catalyst and will approximately be 2 to 5% of the carbon balance.

The effluent stream exiting the MTO reactor will typically be at a relatively high temperature of 350° to 600° C. (662° to 1112° F.) and must be substantially cooled prior to entering a phase separation zone. Typically, this cooling is done either by heat exchange against the feed methanol stream or by the use of an aqueous quench stream in a quenching tower or a combination of both of these techniques. Regardless of the heat exchange technique that is used, it is preferred to substantially cool and condense at least a substantial portion of the water by-product contained in the effluent from the conversion zone utilizing a quench tower operated with a cool quenching medium consisting essentially of water and at quenching conditions whereby the effluent stream is partially condensed with recovery of a substantial portion of the water by-product of the MTO conversion zone. The quench tower usually operates at a pressure which is approximately 40 to 95% of the pressure maintained in the MTO conversion zone and the overhead recovered from this quench tower will still contain substantial amounts of water vapor along with the hydrocarbon and oxygenate products of the synthesis reaction. A preferred two stage quench tower design for this opeartion is shown in my recently issued patent, U.S. Pat. No. 6,403,854, all of the teaching of which are hereby incorporated herein by referenece. It is preferred to take this overhead stream from the quench tower and run it through a series of suction drums and compressors in order to elevate its pressure to a range of about 2000 kPa (290 psi) to 2600 kPa (377 psi).

Referring now to the attached FIG. 1 for details of the product recovery scheme of the present invention, it shows a schematic outline of the interrelationship and interconnection between the various zones of a preferred embodiment of the present invention. Zone 1 is the MTO conversion zone and it is charged with a methanolic feedstock that enters the system via line 9. Zone 1 is operated in accordance with the teachings set forth above to produce an effluent stream which exits zone 1 via line 12 and is charged to the lower region of quench zone 2 wherein it is countercurrently contacted with a cooled circulating aqueous stream in order to condense a substantial portion of the significant water by-product that is produced in the MTO reaction zone. Zone 2 is shown with an aqueous quenching medium being withdrawn via line 14 and recirculated to the upper region of quench zone 2 after passage through a suitable cooling means (not shown). A portion of the circulating aqueous stream in the quench zone is withdrawn via line 14 and passed to oxygenate recovery zone 3 which operates to strip substantially all oxygenates that are dissolved in the circulating aqueous scrubbing medium and to recover and recycle these oxygenates to MTO zone conversion zone 1 via lines 16 and 9. A water stream which is substantially free of contaminants is withdrawn from zone 3 via line 17 and is the principal outlet for the water by-product. The resulting cooled and quenched overhead vapor stream recovered from quench zone 2 via line 13 is then compressed by means not shown to a pressure range previously specified and charged to primary product separating zone 4 which is operated at approximately 10° to 100° C. (50° to 212° F.) and preferereably about 20 to 66° C. (68° to 151° F.) to produce a three-phase separation. The vapor stream recovered from the three-phase separator 4 is withdrawn therefrom via line 22 and passed to the lower region of primary DME absorption zone 6. The liquid hydrocarbon phase that forms in zone 4 has substantial amounts of DME, light olefins and unreacted methanol dissolved therein and it is passed via line 25 into stripping zone 5 where it contacts an upflowing vapor stream generated by a reboiler (not shown) under stripping conditions effective to remove DME and light olefins from this hydrocarbon stream and generate an overhead vapor stream recovered by means of line 26 containing DME, ethylene and propylene along with minor amounts of light saturates that are dissolved in this relatively heavy hydrocarbon stream. The liquid hydrocarbon stream withdrawn from the bottom of DME stripping zone 5 is passed therefrom via line 27 and constitutes a heavy hydrocarbon by-product stream of the MTO reaction which essentially consists of $C_4$, $C_5$ and $C_6$ Olefins in admixture with a minor amount of $C_4^+$ saturates. In the preferred MTO operation with a SAPO-34 catalyst system, this heavy liquid hydrocarbon stream withdrawn via line 27 will comprise approximately 8 to 18% of the methanol equivalent carbon value charged to MTO conversion zone 1.

At the intersection of line 26 with line 22, at least a portion of the hydrocarbon vapor stream from separation zone 4 is combined with at least a portion of the overhead vapor stream produced in the DME stripping zone 5 to form a DME-rich light hydrocarbon vapor stream which is charged via line 22 to the lower region of a primary DME absorption zone 6. Primary DME absorption zone 6 is a conventional liquid-gas contacting zone packed with a suitable material well known to those skilled in the art to enhance vapor liquid interaction as the ascending vapor stream meets a descending liquid stream. Suitable contacting means are various shaped packing materials that are well known to those skilled in the art as well as vapor liquid contacting trays such as the well-known multi-downcomer trays that are available from UOP. The solvent charged to DME scrubbing zone 6 is in accordance with the present invention is a portion of the methanolic feedstock that enters the flow scheme via line 9 and flows via line 10 to the upper region of absorption zone 6 wherein it is passed into countercurrent contact with upflowing DME-rich light hydrocarbon vapor stream which is charged to scrubbing zone 6 via line 22. The packing material used in scrubbing zone 6 is typically a Rashig ring material which is inert to the various active ingredients charged to scrubbing zone 6 and has a high mass transfer efficiency for promoting interaction between the upflowing vapor stream and the descending methanolic solvent stream. Scrubbing zone 6 is operated at scrubbing conditions effective to produce a liquid solvent bottom stream containing methanol, DME, water and substantial and undesired amounts of ethylene and propylene and a light olefin-rich, DME-lean and methanol-containing overhead vapor stream. Preferably, the scrubbing conditions encompass a pressure of about 1896 to 2241 kPa (275 to 325 psi) and a temperature of about 20° to 66° C. (68° to 151° F.) where the pressure is measured at the top of the column where the overhead vapor stream is withdrawn via line 19 and the temperature is measured at the bottom of the column where the DME-rich solvent is withdrawn via line 20. The vapor to liquid loading used in scrubbing zone 6 is of course a function not only of the concentration of methanol in the solvent charged to the top of zone 6 via line 11 but also the concentration of DME in the inflowing vapor stream charged to the bottom of this zone via line 22. As indicated above, the methanolic feed stream to the MTO conversion zone is typically available in a concentrated form of up to 99 mass-% methanol or higher. However, in some cases, where the economics dictate the use of a crude methanol stream as the feed stream to the MTO conversion zone, the methanolic content maybe reduced to as low as 80 mass-% methanol. The methanolic solvent that is charged to scrubbing zone 6 by means of lines 9 and 10 may then have a methanol concentration of about 80 to 99.9 mass-% methanol and preferably will have about 95 to 99.9 mass-% methanol when a concentrated methanolic feed is charged to the MTO conversion zone. The DME concentration in the vapor stream entering zone 6 via line 22 may range from about 0.5 to about 2.5 mass-% of the total vapor stream. Considering then the range of these variable factors, it is appropriate to run scrubbing zone 6 at a solvent-to-vapor mass ratio of about 1:1 to 3:1with the best results obtained with a solvent-to-vapor mass ratio of about 1.2:1 to 2.5:1. The exact choice of the solvent-to-vapor mass ratio used in zone 6 is selected from the ranges specified to preferably eliminate 85 to 99.99 wt-% of the DME that enters the zone via line 22. Best practice for a methanolic solvent that contains 99.5 mass-% methanol or higher is to use a solvent-to-vapor loading selected from the ranges specified to remove 95 to 99.9 wt-% of the DME entering the zone via line 22.

At least a portion of the DME-lean light olefin-rich and methonal-containing overhead vapor stream from primary DME scrubbing zone 6 is then in accordance with the present invention passed via line 19 to the lower region of secondary absorption zone 8 in order to remove residual methanol vapor therefrom. Since the operation of scrubbing zone 6 necessarily results in a vapor stream that is saturated with methanol at the conditions prevailing at the top of zone 6 this stream will contain about 1.5 to 5.5 mass-% methanol. In order to recover this small amount of methanol dissolved in the overhead vapor stream withdrawn from zone 6, it is passed via line 20 to the middle region of zone 8 wherein it is scrubbed free of methanol with a portion of the by-product water stream recovered in oxygenate recovery zone 3 which flows to zone 8 via lines 17 and 18. The details of the operation of zone 8 will be described below.

Figure 2:
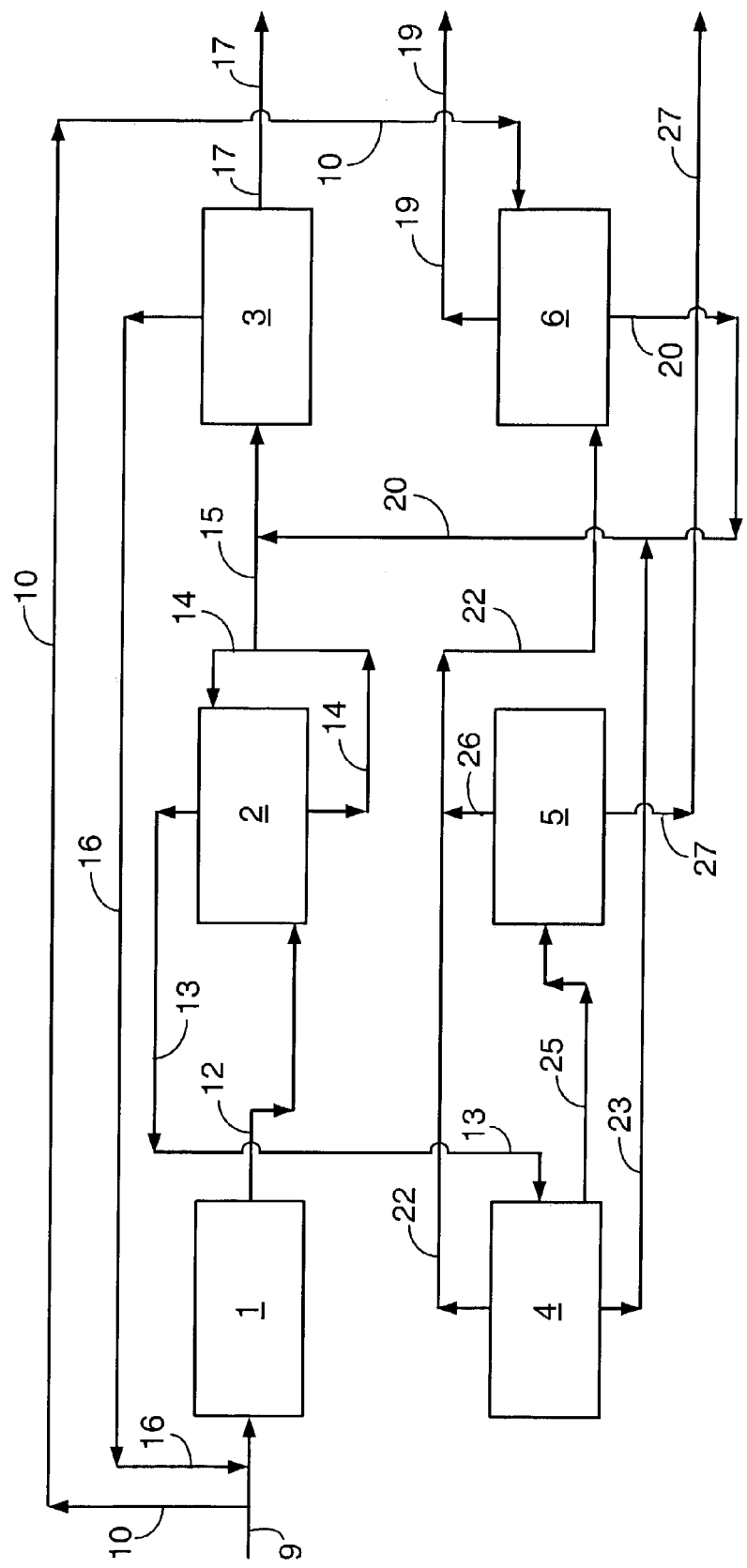

Returning to the liquid solvent bottom stream recovered from scrubbing zone 6 via line 20, it contains methanol, DME, water and substantial and undesired amounts of ethylene and propylene. In the prior art flow scheme shown in FIG. 2 of U.S. Pat. No. 4,587,373, the liquid product stream from the DME absorber 22 is shown as being passed into a separator wherein an aqueous phase is separated from a liquid hydrocarbon phase which is then returned to the DME stripping zone 26 which operates on the liquid hydrocarbon stream recovered from the primary separator. It was apparently unappreciated in the prior art that despite this phase separation, the methanolic-rich solvent stream still contains substantial amounts of dissolved ethylene and propylene which, when they are recycled to the MTO conversion zone via oxygenate stripper 18 of the '373 patent, can cause substantial internal recycle of these very reactive materials with resulting increase in size of the MTO conversion zone as well as decrease in stability of the catalyst system due to undesired polymerization and condensation of these very reactive light olefin materials. In fact, for a DME scrubbing zone operated as specified for zone 6 of the present invention, the DME-rich liquid solvent withdrawn from the bottom of the zone via line 21 even after phase separation will have dissolved therein approximately 10 to 15 mass-% of the ethylene that enters zone 6 via line 22 and about 35 to 50 mass-% of the propylene that is charged to this column. The existence and magnitude of this internal light olefin recycle stream was apparently not recognized or appreciated in the flow scheme that is shown in FIG. 2 of the '373 patent.

In accordance with the present invention, at least a portion of the liquid solvent bottom stream recovered from scrubbing zone 6 is passed via line 20 to light olefin stripping zone 7 which is operated at a severity level sufficient to lift a substantial portion of the ethylene and propylene contained in this aqueous liquid solvent bottom stream without stripping any significant portion of the methanol therefrom to produce a stripper overhead stream containing DME, ethylene and propylene and an aqueous bottom stream containing DME, methanol, water and reduced amounts of light olefin relative to the olefin content of the liquid solvent bottom stream charged to this zone 7 by means of line 20. It is preferred to operate this light olefin stripping step at a severity level which is sufficient to lift a substantial portion of the light olefins while simultaneously maintaining substantially all (i.e. at least 90% or more) of the methanol contained in the input liquid solvent stream in the liquid solvent bottom stream recovered from zone 7. In particular, the severity level is preferably set such that 95 to 99 mass-% of the methanol entering stripping zone 7 via line 20 leaves this zone in the light olefin-lean bottom liquid stream withdrawn therefrom via line 21. This stripping zone must however be operated at a severity level which is sufficient to lift a substantial portion of the light olefins contained in the liquid stream entering the zone via line 20. Ordinarily, the severity level measured in terms of temperature, pressure and stripping rate is set to produce an aqueous bottom stream from zone 7 containing less than 1 mass-% ethylene with best results when the severity levels are set such that the bottom stream contains less than 0.25 mass-% ethylene. It is to be noted that the operation of light olefin stripping zone 7 may use a reboiler (not shown) in order to generate the upflowing vapor streams in a quantity necessary to strip the light olefins or as is shown in the drawing an optional light olefin-free gas stream may be injected into the bottom of stripping zone 7 via line 11 in order to provide the necessary stripping medium. It is of course within the scope of the present invention to operate stripping zone 7 with a combination of a stripping medium generated via a reboiler (not shown) along with olefin depleted stripping gas which enters zone 7 via line 11. The oxygenate-rich and light olefin-lean liquid stream that is withdrawn from the bottom of light olefin stripping zone 7 via line 21 is then recycled via line 9 back to the MTO conversion zone in order to provide additional reactants for conversion therein.

The light olefin-containing vapor stream withdrawn from stripping zone 7 via line 28 will contain minor amounts of DME that co-boil with the propylene material contained therein and consequently needs to be furthered treated in order to remove this DME. This stream will contain an amount of methanol dictated by the methanol liquid-vapor equilibrium maintained at the top of stripping zone 7. This vapor stream will consequently also contain about 1.5 to 5.5 mass-% methanol along with the small amount of DME. In accordance with the present invention a substantial portion of the overhead vapor stream withdrawn from light olefin stripping zone 7 is passed via line 28 to the lower region of secondary DME absorption zone 8 wherein this vapor stream is brought into intimate contact with a descending liquid stream containing an aqueous solvent. In view of the facts that the mass flow and DME concentration in this vapor stream entering zone 8 via line 28 are much less than the corresponding numbers for the vapor stream that enters the primary scrubbing zone 6 via line 22, and that the opportunities for utility savings are much greater, best practice is to use the lower region of secondary DME scrubbing zone 8 to absorb DME and methanol from this overhead vapor stream. The solvent used in secondary DME scrubbing zone 8 is a portion of its substantially pure by-product water stream recovered in oxygenate recovery zone 3 and it flows to the upper region of zone 8 via lines 17 and 18. The contacting means used in zone 8, in order to promote intimate contact between the ascending vapor stream with the descending solvent stream, are preferably the same as utilized in zone 6 and the scrubbing conditions used in zone 8 will include a solvent-to-vapor mass ratio of about 2:1 to 5:1. Recalling that at least a portion of the DME-lean, light olefin-rich and methanol containing overhead vapor stream from primary DME scrubbing zone 6 is also charged to zone 8 via line 19 it is clear that this zone is dual-functional. It is designed to not only clean-up the residual amount of DME that is present in the overhead vapor stream entering this zone via line 28 but also to remove residual methanol from both vapor streams that are charged to this zone. According to the present invention this dual-functionality of zone 8 is enabled by the fact that the methanol contained in both streams has a high affinity for the aqueous solvent and once the methanol content of the aqueous solvent starts to increase it in turn increases the capacity of this solvent to dissolve DME, thereby generating an effective DME solvent in situ. In order to take maximum advantage of this finding, it is preferred to separate the points of entry of these two vapor stream into zone 8 such that the stripper overhead stream in line 28 that contains DME enters the bottom region of zone 8 and the primary DME scrubber overhead stream in line 19 enters the middle region of zone 8. It is even more preferred that the points of entry of these two overhead stream into zone 8 be separated by at least one or more theoretical plate in order to ensure that solvent entering the lower region of this zone contain a substantial quantity of methanol. Best practice is to separate these two vapor entry points by at least 2 to 5 theorectical plates.

Secondary DME scrubbing zone 8 is operated at scrubbing conditions selected to produce a DME-lean and methanol-lean overhead vapor product stream containing ethylene and propylene withdrawn by means of line 29 and a bottom liquid stream containing DME, methanol and water which is preferrably recycled via lines 24 and 15 to oxygenate recovery zone 3 wherein the oxygenates contained therein are stripped and recycled to zone 1 via lines 16 and 9 to provide additional quantities of reactant thereto. It is a preferred practice to pass the DME-lean overhead hydrocarbon vapor product stream withdrawn from zone 8 via line 29 to downstream facilities (not shown) in order to further purify this stream and recover polymer-grade ethylenes and propylenes.

The following examples are presented in order to facilitate further understanding of the present invention in reference to a control example. They are however presented for purposes of illustration rather than limitation. These examples will contrast the results using the product recovery scheme of the present invention with those obtained via the product recovery scheme taught in the prior art. The product recovery scheme of the present invention is shown in FIG. 1 and the product recovery scheme of the prior art is shown in FIG. 2. A comparison between the two figures will show that, to the extent possible, common elements between the two product work-up flow schemes use identical numbers in order to make direct comparison easier. In both of the examples, the MTO conversion zone is run in a fluidized bed mode of operation with a SAPO-34 type of catalyst. The SAPO-34 catalyst is prepared in accordance with the teachings of U.S. Pat. No. 5,191,141 and is used in a particle size appropriate for fluidization (i.e. average particle size diameter is about 70 to 80 microns). The catalyst particle formulation used in both of these examples is based on a 40 mass-% SAPO-34 molecular sieve bound with 60 mass-% of inert filler/binder materials.

The feed stream charged to the MTO conversion zone 1 via line 9 in both cases comprises a mixture of methanol and water containing 99.85 wt-% methanol. No diluent is used in either of these examples but substantial amounts of a steam diluent is autogenously generated due to the very rapid kinetics associated with the formation of intermediate DME.

The operating conditions used in zone 1 in both cases are as follows: (1) feed stream entry temperature of about 100° C. (212° F.) and an effluent exit temperature of about 475° C. (887° F.); (2) a pressure of about 239 kPa (34.7 psi); (3) a WHSV of 2.4 $hr^{-1}$ based on mass of total catalyst with the catalyst being recirculated after product separation in a conventional manner primarily via internal or external catalyst recycle means; and (4) a catalyst draw-off rate for regeneration from the circulating inventory of catalyst in zone 1 in amounts sufficient to maintain an average catalyst coke content of the circulating inventory of catalyst in the range of about 2 to 5 mass-%. The drawn-off catalyst is oxidatively regenerated in an associated conventional regenerator (not shown in either of the attached drawings) to reduce coke level to about 1 mass-% or less and the resulting regenerated catalyst is recirculated to the MTO conversion zone in order to maintain the specified average coke level on the circulating catalyst inventory.

Operation of zone 1 in both of these examples at these conditions with the specified catalyst system and the methanol feedstock results in 99.5 mass-% conversion based on methanol disappearance and the yield structure shown in Table 1 based on an appropriate carbon balance.

Because methanol contains about 56 mass-% bound water, water is a very substantial by-product of the MTO reaction that occurs in zone 1 and substantial amounts of water must be condensed out of the effluent stream and separated from the hydrocarbon products of the MTO reaction zone in order to prepare the portion of effluent stream which is charged to the product recovery flow scheme in both of these examples.

TABLE 1

Yields from MTO Conversion Zone

| Component | Selectivity (Mass-% of Methanol Equivalent) |
| --- | --- |
| Methane | 0.85 |
| Ethylene | 33.50 |
| Ethane | 0.65 |
| Propylene | 44.50 |
| Propane | 0.30 |
| Butylene | 9.5 |
| Butane | 0.01 |
| $C_{5+}$ | 5.00 |
| Coke | 2.85 |
| Unreacted Methanol | 0.50 |
| DME | 1.05 |
| Others ($H_2$, CO, $CO_2$, Dienes) | 1.29 |
| TOTAL | 100.0 |

The effluent stream exiting MTO conversion zone 1 via line 12 can be subjected to conventional cooling procedures such as feed/effluent heat exchange (not shown) and is charged to quench zone 2 wherein it undergoes further cooling in order to condense a substantial amount of the by-product water contained therein. Quench zone 2 operates as previously described with a circulating quenching medium which is primarily water and countercurrently contacts the hot, steam-rich effluent stream from zone 1 in a manner designed to condense a major portion of the by-product water from the MTO conversion step and to drop the temperature of this effluent stream such that the hydrocarbon portion leaves zone 2 via line 13 at a temperature of about 40° C. (104° F.) and a pressure of about 200 kPa (29 psi). In both of the examples, a portion of the circulating aqueous medium in line 14 is drawn off via line 15 and passed to oxygenate recovery zone 3. Zone 3 operates at conventional oxygenate stripping conditions in order to strip substantially all oxygenates which are then recycled to MTO conversion zone 1 via lines 16 and 9. These oxygenate materials accumulate in this circulating quenching medium due to their high solubility therein. An aqueous stream withdrawn from the lower region of oxygenate recovery zone 3 via line 17 is substantially pure water with very minor amounts of contaminants dissolved therein.

The hydrocarbon and oxygenate-containing vapor overhead from the top of quench zone 2 is passed via line 12 into the primary product separation zone 4. During the passage of this vapor stream from zone 2 to zone 4, it is passed through a series of suction drums, compressors and coolers (not shown in the attached drawing) to increase its pressure to about 2069 kPa (300 psi) and as a result, it enters primary product separator zone 4 at a temperature of about 38° C. (100° F.) and is held at these conditions in zone 4 in order to produce a three-phase separation whereby a hydrocarbon-rich vapor phase is withdrawn from zone 4 via line 22, a heavy hydrocarbon liquid phase is withdrawn from the zone via line 25 and an aqueous phase is withdrawn therefrom via line 23. In FIG. 1 used in Example 1, the aqueous phase from zone 4 is withdrawn therefrom via line 23 and passed via lines 23, 24 and 15 into oxygenate recovery zone 3. In the flow scheme shown in FIG. 2 used in Example 2, this aqueous stream from the primary product separator is also passed to zone 3 except in this case, it travels via lines 23, 20 and 15 to oxygenate recovery zone 3.

In both Examples 1 and 2, the hydrocarbon liquid phase that is withdrawn from primary product separating zone 4 via line 25 is passed to DME stripping zone 5 which operates at a pressure at the top of the stripper where the overhead is withdrawn which is 172 kPa (25 psi) less than the pressure maintained in zone 4. DME stripping zone 5 uses a reboiler (not shown in either drawing) in order to generate upflowing vapors that in both cases lift DME and light olefins dissolved in the hydrocarbon input stream into the overhead stream which is withdrawn from this zone via line 26 and flows to the junction with line 22 wherein it is combined with the overhead from zone 4. The resulting mixture is then passed into primary DME scrubbing zone 6 via line 22. A liquid hydrocarbon stream which is rich in $C_4^+$ material is withdrawn from the bottom of zone 5 by means of line 27 in both Examples 1 and 2. This bottom stream comprises the $C_4$ and $C_5$ olefin products of the MTO conversion zone along with various other heavier hydrocarbon by-products. This heavy hydrocarbon product stream is withdrawn via line 27 and passed to further heavy hydrocarbon treatment facilities that are located downstream from the MTO process.

In the flow scheme of the present invention used in Example 1 as well as the flow scheme of the prior art used in Example 2, zone 5 provides an additional means of DME recovery and also light olefin recovery. The overhead vapor stream that is separated in primary product separator 4 is combined with the overhead vapor stream from stripping zone 5 at the junction of lines 22 and 26 in both cases and the resulting combined vapor stream flows via line 22 to the lower region of primary DME absorption zone 6. It is to be recognized that because of pressure differences between the vapor streams present in line 22 and line 26, a compressor may be needed in line 26 to ensure that the flow of the DME overhead stream from zone 5 is as described.

The product recovery scheme of the present invention (shown in FIG. 1) and that of the prior art (shown in FIG. 2) both utilize a methanolic-rich solvent in a scrubbing zone 6 in order to remove DME from the light hydrocarbon products of the MTO conversion reaction. The methanolic solvent is obtained in both cases as a portion of the methanolic feed stream which enters the process via line 9. The portion that is used in scrubbing zone 6 is diverted in line 10 and passes into the upper region of scrubbing zone 6 wherein it flows in countercurrent fashion against the upflowing combined hydrocarbon-containing vapor stream which enters the lower region of zone 6 via line 22. The amount of methanolic solvent that is diverted via lines 9 and 10 for use in scrubbing DME and other oxygenates from the light hydrocarbon vapors injected into the bottom of zone 6 via line 22 is about 50 to 100 mass-% of the total feed that is charged to the MTO conversion process via line 9. In both cases, zone 6 is operated at DME scrubbing conditions including a temperature of 54.4° C. (130° F.), a pressure of 2020 kPa (293 psi) and a solvent-to-vapor mass ratio of about 1.32:1 to produce a DME-lean and light hydrocarbon-rich overhead vapor stream, which in both cases exits zone 6 via line 19 and a DME-rich methanolic solvent liquid stream which exits zone 6 via line 20. The temperature and pressure of zone 6 as recited above are measured at the point of withdrawal of the overhead vapor stream.

Having completed a description of the common elements of the flow scheme that is used in both Examples, the following two examples are structured to make manifest the differences between the operation of the flow scheme of FIG. 1 an embodiment of the present invention used in Example 1 and of the prior art scheme FIG. 2 used in Example 2.

EXAMPLE 1

Present Invention

The product recovery flow scheme utilized in this example is shown in FIG. 1 in this embodiment, primary DME scrubbing zone 6 operates as described above in the discussion of the common elements between the two flow schemes to produce an overhead vapor stream withdrawn by means of line 19 which is DME-lean and $C_2$ and $C_3$ olefin-rich. Because this light olefin-rich vapor stream also contains an amount of methanol dictated by the vapor-liquid equilibrium conditions maintained at the top of zone 6, it is charged via line 19 to the middle region of secondary DME recovery zone 8 where this overhead vapor stream from zone 6 countercurrently contacts an aqueous solvent stream under conditions selected to scrub substantially all of the methanol from this vapor stream. The aqueous solvent used in secondary DME recovery zone 8 is provided to this zone via lines 17 and 18 and is a portion of the by-product water stream that is produced in zone 3. In accordance with the present invention zone 8 also performs the final polishing of the overhead vapor stream produced in light olefin stripping zone 7 which flows to zone 8 by means of line 28. The entry point of this second overhead stream is in the lower region of zone 8 since this second overhead stream contains not only methanol but also a minor amount of DME that co-boils with the propylene contained therein as explained previously. In accordance with a preferred embodiment of the present invention the entry points into zone 8 for these two overhead vapor streams are separated by a vertical distance which corresponds to at least one or more theoritical plates. This separation of entry points for the two overhead streams that are scrubbed in zone 8 facilitate the recovery of both DME and methanol in the bottom region of this zone since the descending aqueous solvent entering the lower region of zone 8 will have a significant methanol content acquired by absorption from the overhead vapor stream charged to this zone via line 19. Since methanol has a high affinity for DME, the aqueous solvent containing methanol entering the lower region of zone 8 (i.e. below the entry point of line 19) is a highly effective solvent for DME and prevents any significant DME contamination of the light olefin product stream withdrawn from zone 8 via line 29. Zone 8 contains suitable contacting means to promote the interaction of the aqueous solvent stream injected via line 18 with the two upflowing vapor streams one of which enters the middle region of zone 8 via line 18 and one of which enters the bottom of zone 8 via line 28. Zone 8 operates at a temperature of about 25° C. (77° F.), a pressure of about 1813 kPa (263 psi) and a solvent-to-total-vapor mass loading ratio of about 5:1. Zone 8 therefore operates to eliminate substantially all DME and methanol from the light olefin product stream of the present invention which is produced as an overhead stream and is withdrawn from this zone via line 29 and constitutes the principal light olefin product stream of the product recovery scheme of the present invention. The DME and methanol-containing aqueous solvent stream that is withdrawn from the bottom of zone 8 is recycled to zone 3 via lines 24 and 15 in order to eventually return the DME and methanol values contained therein to zone 1 via lines 16 and 9.

Returning to the operation of zone 6, the methanolic solvent stream which is rich in DME that is withdrawn from zone 6 via line 20 is in accordance with the present invention charged to light olefin stripping zone 7 and enters this zone at or below the mid-point thereof. Light olefin stripping zone 7 operates in accordance with the present invention at a severity level which is sufficient to strip a substantial portion of the $C_2$ and $C_3$ olefins contained in the DME-rich solvent stream that is charged to this zone via line 20 but insufficient to remove a significant portion of the methanol that is contained in this solvent stream. In other words, the severity used in zone 7 is substantially less than the severity level that is used in oxygenate recovery zone 3 where it is desired to lift substantially all oxygenates into the overhead vapor stream. Zone 7, as previously explained, can operate with a stripping gas medium which is olefin-lean and rich in methane which can enter zone 7 via line 11. Alternatively, zone 7 can operate with a reboiler (not shown) and autogenously generate upflowing vapors by reboiling a portion of the light olefin-depleted methanol solvent that is withdrawn from the bottom of this zone via line 21. For purposes of this example, line 11 is blocked off and a reboiler system is used to generate upflowing vapors with a suitable heat recovery means (not shown) located in line 28 to minimize the utilities associated with this reboiling operation. In this example, zone 7 is operated at conditions which are sufficient to strip substantially all of the ethylene contained in the DME-rich solvent that is charged to this zone. These conditions include a pressure of 1827 kPa (265 psi) and a temperature of 76.7° C. (170° F.) which conditions are measured at the point of withdrawal of the overhead vapor stream from zone 7 via line 28. Under these conditions, zone 7 operates to remove 100% of the ethylene present in the DME-rich methanolic solvent charged thereto via line 20 and 51.2% of the propylene which is dissolved in the DME-rich methanolic solvent. The resulting light olefin-rich vapor overhead stream which is withdrawn from zone 7 via line 28 is unfortunately contaminated with a minor amount of DME due to the strong affinity between DME and propylene. It is in accordance with the present invention this overhead vapor stream is passed via line 28 to the lower region of secondary DME scrubbing zone 8 in order to scrub methanol and the contaminating DME therefrom. The bottoms stream from zone 7 is withdrawn therefrom via line 21 and is a light olefin-lean, DME-rich methanolic stream which is returned to MTO conversion zone 1 via lines 21 and 9.

The calculated separation recovery efficiencies associated with the embodiment of the present invention described in this example are presented in Table 2 in tabular form wherein the first column shows the principal products and methanol (includes both unreacted and solvent methanol), the second column shows the percentage of this product that is recovered in the recycled liquid solvent stream 21 and in the recycled liquid aqueous stream 24 and the third column presents the percentage of the product that is recovered in the light olefin product stream withdrawn from the instant product recovery method via line 29. By reference to the second line of Table 2, it can be shown that the present invention drives the ethylene recovery efficiency of the product recovery flow scheme to 100% which stands in sharp contrast to the prior art recovery rate of 87.71% which is hereinafter shown in Table 3.

TABLE 2

Separation and Recovery Efficiencies* for Product Recovery Flow Scheme of Present Invention

| MTO Reactant and Reaction Products | % Recovered in Recycle Streams | Recovered in Product Stream |
|---|---|---|
| Methane | 0 | 100 |
| Ethylene | 0 | 100 |
| Ethane | 0 | 100 |
| Propylene | 20.0 | 80.0 |
| Propane | 19.13 | 80.87 |
| DME | 99.20 | 0.80 |
| Methanol** | 99.90 | 0.10 |

*Measured in mass-% of the MTO reaction product or reactant recovered on a per pass basis.
**Includes both unreacted methanol present in effluent stream 12 as well as methanol solvent directed to scrubbing zone 6 via lines 9 and 10.

With reference to the fourth line of Table 2, it can be seen that the propylene recovery rate increases to 80% which stands in contrast to the 59.72% recovery rate associated with the prior art flow scheme hereinafter exemplified in the control Example 2. It is to be noted that this increase in recovery efficiencies for the desired light olefin was not accompanied by any sacrifice in the efficiency of DME recovery which is clearly demonstrated by comparing the results of the DME recovery efficiencies from Tables 2 and 3. The methanol recovery numbers given in the last line of Table 2 shows the substantial improvement in recovery of this reactant that is enabled by the two stage scrubbing procedure of the present invention.

EXAMPLE 2

Control

With reference now to the details associated with operations of DME scrubbing zone 6 in FIG. 2 in accordance with the teachings of U.S. Pat. No. 4,587,373, it can be seen that the DME-rich methanolic solvent that is withdrawn from the bottom of zone 6 is passed via line 20 and line 15 to oxygenate recovery zone 3 in order to strip both the recovered DME and the methanolic solvent from any water that is present in this stream and to recycle the resulting DME intermediate and unreacted methanol to zone 1 via line 16. It is to be noted that the DME-rich methanolic solvent that is withdrawn from zone 6 via line 20 can be passed into a phase separator (not shown) in a conventional manner in order to allow recovery of any relatively high boiling hydrocarbons (i.e. $C_4+$ material) that condense in zone 6 due to the conditions maintained therein. The DME-lean light olefin-containing vapor product stream is then withdrawn from the upper region of scrubbing zone 6 via line 19 and passed to further downstream processing not a part of the MTO process of the '373 patent. This product stream also contains a significant amount of methanol dictated by the vapor-liquid equilibrium conditions maintained at the top of zone 6. In this case these conditions results in the overhead vapor stream containing 2.15 mass-% of the total methanol charged to zone 6 in the form of solvent methanol entering via line 10 and unreacted methanol via line 22.

FIG. 2 is intended to represent the flow scheme that is shown in FIG. 2 of U.S. Pat. No. 4,587,373. In FIG. 2 of the '373 patent, zone 12 corresponds to zone 1 of the attached FIG. 2 and is the MTO conversion zone. Quenching zone 2 is functionally represented by cooling zone 14 of the '373 patent. The oxygenate recovery zone 3 of the attached FIG. 2 corresponds to oxygenate stripper 18 of the '373 patent. Primary product separator 4 corresponds to product separator 16 of the '373 patent. DME stripping zone 5 is represented in FIG. 2 of the '373 patent by stabilizer tower 26 and DME scrubbing zone 6 is represented by DME absorber 22.

By utilizing the operating conditions hereinbefore specified, the MTO conversion yields shown in Table 1 and the known affinity for DME exhibited by a rich methanolic solvent, the separation and recovery efficiencies associated with the prior art product recovery flow scheme were calculated utilizing a conventional chemical process flow scheme simulation program (which was also used in the calculation presented in Table 2). The results of these calculations are presented in Table 3 in terms of separation and recovery efficiencies for methanol and the various key products of the MTO conversion zone.

TABLE 3

Separation and Recovery Efficiencies* for Prior Art Product Recovery Flow Scheme

| MTO Reactant and Reaction Product | % Recovered in Recycle Stream | % Recovered in Product Stream |
|---|---|---|
| Methane | 3.43 | 96.57 |
| Ethylene | 12.29 | 87.71 |
| Ethane | 11.77 | 88.23 |
| Propylene | 40.28 | 59.72 |
| Propane | 40.99 | 59.01 |
| DME | 99.0 | 1.0 |
| Methanol** | 97.85 | 2.15 |

*Measured in mass-% of the MTO reaction product or methanol recovered on a per pass basis.
**Includes both unreacted methanol and solvent methanol.

The efficiencies recited in Table 3 are measured in terms of mass-% of methanol entering zone 6 and of the particular MTO reaction product that is specified in the first column that is recovered in the product separation system on a per pass basis. For example, in the case of ethylene, the results show that 87.71 mass-% of the ethylene produced in MTO conversion zone 1 is recovered in the overhead stream 19 from DME scrubbing zone 6 which in the light olefin product stream for the '373 patent. In contrast, the remaining portion of the ethylene is dissolved in the methanolic-rich solvent withdrawn from the bottom of scrubbing zone 6 via line 20 and recycled to MTO conversion zone 1 via lines 22, 15 to zone 3 and then via lines 16 and 9. The results for propylene are even more interesting in that 59.72 mass-% of the propylene produced in zone 1 exits the process via line 19 as part of the light olefin product stream of the product recovery system illustrated in FIG. 2. Quite surprisingly however, a substantial portion of the propylene finds its way back to MTO conversion zone 1 because of its high solubility in the methanolic solvent used in DME scrubbing zone 6. The recycled propylene travels via lines 20 and 15 into zone 3 wherein it is stripped into the overhead stream exiting zone 3 via line 16 wherein it is ultimately returned to MTO conversion zone 1 via lines 16 and 9.

The principal lesson to be learned from an examination of the results of the calculations presented in Table 2 is that the use of a methanolic solvent in DME scrubbing zone 6 has the unintended consequence of dragging substantial amounts of $C_2$ and $C_3$ olefins into an internal recycle stream where they are returned to MTO conversion zone 1 and ultimately creates a light olefin internal circuit in the flow scheme that builds up the concentration of these materials in stream 12 until the amounts that exit the system via line 19 balance the amounts that are produced in MTO reaction zone 1. This light olefin recycle circuit that therefore occurs in the flow scheme of the '373 patent is an unintended consequence of using methanol as the solvent in the scrubbing zone in order to take advantage of methanol's well-known high affinity for DME.

By contrasting the results shown in Table 2 with those presented in Table 3, it is evident that the instant invention eliminates a significant loss of methanol in the light olefin product stream and enables a substantial reduction in the rate of recycle of light olefins that is necessary to recover 100% of the desired light olefin products which are produced in MTO conversion zone 1. The degree of improvement associated with the embodiment of the present invention shown in Example 1 over the prior art flow scheme exemplified in Example 2 is highlighted in Table 4 which presents the recycle ratio required to recover 100% of the two desired light olefin products of the MTO reaction step in terms of the recycle ratio necessary for each of these products to force 100% of the product from zone 1 to exit the system via line 29 in the case of FIG. 1 and via line 19 in the case of FIG. 2.

TABLE 4

Recycle Ratio* Required to Recover 100% of the $C_2$ and $C_3$ Olefin Products of MTO Reaction Step**

| Product | Prior Art Flow Scheme | Present Invention Flow Scheme | Improvement |
|---|---|---|---|
| Ethylene | 1.14 | 1.0 | 12.3% |
| Propylene | 1.694 | 1.25 | 26.2% |

*(Recycle + Feed)/Feed
**Basis is amount of product that must be recycled to result in 100% recovery of that product on a per pass basis.

By reference to the first line of Table 4, the instant invention shows an improvement in the recycle ratio parameter of 12.3% for ethylene. The results are even more dramatic with respect to the propylene product of the MTO conversion reaction. As is shown in line 2 of Table 4, the instant invention results in a 26.2% improvement in the recycle ratio. The present invention acts dramatically and convincingly to substantially lower the recycle ratio required in order to recover the highly desired light olefin products. This diminishment of this recycle ratio obviously results in a substantial shrinkage of the size of MTO conversion zone 1 due to the diminished amount of ethylene and propylene that must be recycled through this zone. In addition, the present invention acts to keep substantial amounts of highly reactive light olefins out of the MTO conversion zone, thereby enhancing the stability of the catalyst system contained therein by eliminating substantial amounts of potential coke precursors.

I claim as my invention:

1. A method of selective recovery of a DME-containing recycle stream and a DME-lean, methanol-lean and light olefin-rich product stream from the effluent stream from a MTO conversion zone wherein the effluent stream contains water, methanol, DME, ethylene, propylene and $C_4$ to $C_6$ olefins, which method comprises the steps of:

(a) cooling and separating at least a portion of the effluent stream into an aqueous liquid stream containing methanol and DME, a hydrocarbon liquid stream containing methanol, DME and $C_4$ to $C_6$ olefins and a hydrocarbon vapor stream containing DME, methanol, ethylene and propylene;

(b) stripping DME from at least a portion of the liquid hydrocarbon stream separated in step (a) in a DME stripping zone operated at stripping conditions effective to produce an overhead vapor stream containing DME, methanol, ethylene and propylene and a liquid hydrocarbon bottom stream containing $C_4$ to $C_6$ olefins;

(c) combining at least a portion of the hydrocarbon vapor stream separated in step (a) with at least a portion of the overhead vapor stream produced in step (b) to form a DME-rich light hydrocarbon vapor stream;

(d) charging the resulting DME-rich light hydrocarbon vapor stream to a primary DME absorption zone and therein contacting this vapor stream with a DME selective solvent containing methanol at scrubbing conditions effective to produce (1) a liquid solvent bottom stream containing methanol, DME, water and substantial and undesired amounts of ethylene and propylene and (2) a light olefin-rich, DME-lean overhead vapor stream containing methanol;

(e) passing at least a portion of the liquid bottom stream recovered from step (d) to a light olefin stripping zone operated at stripping conditions effective to strip at least a substantial portion of the ethylene and propylene contained in the liquid bottom stream without stripping any significant portion of the methanol therefrom to produce a stripper overhead stream containing DME, methanol, ethylene and propylene and a liquid bottom stream containing DME, methanol, water and reduced amounts of light olefins relative to the light olefin content of the liquid solvent bottom stream charged to this step;

(f) recycling at least a portion of the liquid bottom stream recovered from step (e) to the MTO conversion zone thereby selectively providing additional oxygenate reactants thereto; and (g) charging at least a portion of the stripper overhead stream from step (e) and at least a portion of the light olefin-rich, DME-lean overhead vapor stream from step (d) to a secondary DME absorption zone wherein these streams are countercurrently contacted with an aqueous solvent at scrubbing conditions selected to produce a DME-lean and methanol-lean overhead vapor product stream rich in ethylene and propylene and a bottom liquid stream containing DME, methanol and the aqueous solvent.

2. The method as defined in claim 1 wherein at least a portion of the aqueous liquid stream separated in step (a) and at least a portion of the bottom liquid stream from step (g) are combined and charged to an oxygenate recovery zone which is operated at oxygenate stripping conditions effective to produce an overhead vapor stream rich in DME and methanol and an aqueous bottom stream which is substantially free of oxygenates and wherein at least a portion of the overhead vapor stream is recycled to the MTO conversion zone thereby providing additional oxygenate reactants thereto.

3. The method as defined in claim 2 wherein the aqueous solvent used in step (g) is at least a portion of the aqueous bottom stream recovered from the oxygenate recovery zone.

4. The method as defined in claim 2 wherein the stripper overhead stream from step (e) that is charged to step (g) enters the secondary DME absorption zone in the bottom region thereof and wherein the light olefin-rich, DME-lean overhead vapor stream from step (d) that is charged to step (g) enters the secondary DME absorption zone at least one or more theoretical plates higher in the zone than the point of entry of the stripper overhead stream.

5. The method as defined in claim 4 wherein the points of entry of the two overhead streams that are charged to the secondary DME absorption zone are separated by at least 2 to 5 theoretical plates.

6. The method as defined in claim 1 wherein the DME-selective solvent used in step (d) contains about 80 to 99.99 mass-% methanol.

7. The method as defined in claim 6 wherein the DME-selective solvent used in step (d) is about 95 to 99.99 mass-% methanol.

8. The method as defined in claim 1 wherein the scrubbing conditions utilized in step (d) include a solvent-to-vapor mass ratio of about 1:1 to 3:1.

9. The method as defined in claim 8 wherein the scrubbing conditions used in step (d) include a solvent-to-vapor mass ratio of about 1.2:1 to 2.5:1.

10. The method as defined in claim 1 wherein the secondary DME absorption zone used in step (g) is operated at scrubbing conditions including a solvent-to-vapor mass ratio of about 2:1 to 5:1.

11. The method as defined in claim 1 wherein the DME-selective solvent charged to step (d) is a portion of the methanol feed stream to the MTO conversion zone.

12. The method as defined in claim 1 wherein the stripping conditions used in step (e) are set to produce a liquid bottom stream containing less than about 1 mass-% ethylene.

13. The method as defined in claim 12 wherein the stripping conditions used in step (e) are set to produce a liquid bottom stream containing less than about 0.25 mass-% ethylene.

14. A method of selective recovery of a DME-containing recycle stream and a DME-lean, methanol-lean and light olefin-rich product stream from the effluent stream from a MTO conversion zone wherein the effluent stream contains water, methanol, DME, ethylene, propylene and $C_4$ to $C_6$ olefins, which method comprises the steps of:
(a) cooling and separating at least a portion of the effluent stream into an aqueous liquid stream containing methanol and DME, a hydrocarbon liquid stream containing methanol, DME and $C_4$ to $C_6$ olefins and a hydrocarbon vapor stream containing DME, methanol, ethylene and propylene;
(b) stripping DME from at least a portion of the liquid hydrocarbon stream separated in step (a) in a DME stripping zone operated at stripping conditions effective to produce an overhead vapor stream containing DME, methanol, ethylene and propylene and a liquid hydrocarbon bottom stream containing $C_4$ to $C_6$ olefins;
(c) combining at least a portion of the hydrocarbon vapor stream separated in step (a) with at least a portion of the overhead vapor stream produced in step (b) to form a DME-rich light hydrocarbon vapor stream;
(d) charging the resulting DME-rich light hydrocarbon vapor stream to a primary DME absorption zone and therein contacting this vapor stream with a DME selective solvent containing methanol at scrubbing conditions effective to produce: (1) a liquid solvent bottom stream containing methanol, DME, water and substantial and undesired amounts of ethylene and propylene and (2) a light olefin-rich, DME-lean overhead vapor stream containing methanol;
(e) passing at least a portion of the liquid solvent bottom stream recovered from step (d) to a light olefin stripping zone operated at stripping conditions effective to strip at least a substantial portion of the ethylene and propylene contained in the liquid solvent bottom stream without stripping any significant portion of the methanol contained therein to produce a stripper overhead stream containing DME, methanol, ethylene and propylene and a liquid solvent bottom stream containing DME, methanol, water and reduced amounts of light olefins relative to the input olefin content of the liquid solvent bottom stream charged to this step;
(f) charging at least a portion of the stripper overhead stream from step (e) and at least a portion of the light olefin-rich, DME-lean overhead vapor stream from step (d) to a secondary DME absorption zone wherein these streams are countercurrently contacted with an aqueous solvent at scrubbing conditions selected to produce a DME-lean and methanol-lean overhead vapor product stream rich in ethylene and propylene and a bottom liquid stream containing DME, methanol and water;
(g) passing at least a portion of the aqueous liquid stream separated in step (a) and at least a portion of the bottom liquid stream produced in step (f) to an oxygenate recovery zone and therein subjecting these streams to oxygenate stripping conditions effective to produce an overhead vapor stream rich in DME and methanol and at aqueous bottom stream which is substantially free of oxygenates;
(h) recycling at least a portion of the liquid solvent bottom streams recovered from step (e) and at least a portion of the overhead vapor stream produced in step (g) to the MTO conversion zone thereby selectively providing additional oxygenate reactants thereto; and
(i) passing at least a portion of the aqueous bottom produced in step (g) to step (f) to provide at least a portion of the aqueous solvent used therein.

15. The method as defined in claim 14 wherein the DME selective solvent charged to step (d) is a portion of the methanol feed stream to the MTO conversion zone.

16. The method as defined in claim 14 wherein the stripper overhead stream from step (e) charged to the secondary DME absorption zone enter this zone substantially below the point of entry of the light olefin-rich, DME-lean overhead vapor stream from step (d).

17. The method as defined in claim 16 wherein the points of entry of the two overhead streams charged to the secondary DME absorption zone are separated by at least one or more theoretical plates.

* * * * *